United States Patent
Wei et al.

(10) Patent No.: US 12,024,530 B2
(45) Date of Patent: Jul. 2, 2024

(54) SENSOR FOR DETECTING GAS ANALYTE

(71) Applicant: CARRIER CORPORATION, Palm Beach Gardens, FL (US)

(72) Inventors: Alexander Wei, West Lafayette, IN (US); Lia Antoaneta Stanciu, West Lafayette, IN (US); Winston Yen-Yu Chen, West Lafayette, IN (US); Aiganym Yermembetova, West Lafayette, IN (US); Benjamin M. Washer, Lafayette, IN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 1037 days.

(21) Appl. No.: 16/811,668

(22) Filed: Mar. 6, 2020

(65) Prior Publication Data
US 2020/0291044 A1 Sep. 17, 2020

Related U.S. Application Data

(60) Provisional application No. 62/816,662, filed on Mar. 11, 2019.

(51) Int. Cl.
| B32B 9/00 | (2006.01) |
| C01B 32/159 | (2017.01) |
| C01B 32/174 | (2017.01) |
| C07F 1/00 | (2006.01) |
| G01N 27/12 | (2006.01) |

(Continued)

(52) U.S. Cl.
CPC ............ *C07F 1/005* (2013.01); *C01B 32/159* (2017.08); *C01B 32/174* (2017.08); *G01N 27/128* (2013.01); *B82Y 15/00* (2013.01); *B82Y 40/00* (2013.01); *C01B 2202/02* (2013.01); *C01B 2202/22* (2013.01); *Y10T 428/30* (2015.01)

(58) Field of Classification Search
CPC ..... B32B 9/007; C01B 32/156; Y10T 428/30; B82Y 30/00; B82Y 40/00
USPC ....................................... 428/408; 423/447.1
See application file for complete search history.

(56) References Cited

U.S. PATENT DOCUMENTS

| 9,739,737 B2 | 8/2017 | Swager et al. |
| 11,428,681 B2 | 8/2022 | Swager et al. |
| 2005/0072213 A1 | 4/2005 | Besnard et al. |

(Continued)

FOREIGN PATENT DOCUMENTS

| CN | 104412100 A | 3/2015 |
| CN | 106415255 A | 2/2017 |
| WO | WO 2015/063341 | * 5/2015 |

OTHER PUBLICATIONS

Chen et al., "Selective Detection of Ethylene by MoS2—Carbon Nanotube Networks Coated with Cu(I)—Pincer Complexes", ACS Sensors, 2020, No. 5, pp. 1699-1706.

(Continued)

*Primary Examiner* — Daniel H Miller
(74) *Attorney, Agent, or Firm* — CANTOR COLBURN LLP

(57) ABSTRACT

A sensor and a method of using the sensor are disclosed. The sensor includes a conductive region in electrical communication with two electrodes, the conductive region including single-walled carbon nanotubes, nanosized particles of a metal dichalcogenide, and a mercaptoimidazolyl metal-ligand complex. The sensor can be used to detect volatile compounds that have a double or triple bond.

10 Claims, 1 Drawing Sheet

(51) Int. Cl.
  *B82Y 15/00*    (2011.01)
  *B82Y 40/00*    (2011.01)

(56) References Cited

U.S. PATENT DOCUMENTS

| | | |
|---|---|---|
| 2013/0273665 A1 | 10/2013 | Swager et al. |
| 2015/0247832 A1 | 9/2015 | Swager et al. |
| 2016/0169810 A1* | 6/2016 | Swager .................. G01N 21/78 436/142 |
| 2016/0276052 A1 | 9/2016 | Shaffer et al. |
| 2020/0291053 A1 | 9/2020 | Wei et al. |
| 2020/0292481 A1 | 9/2020 | Wei et al. |

OTHER PUBLICATIONS

Esser et al., " Selective Detection of Ethylene Gas Using Carbon Nanotube-based Devices: Utility in Determination of Fruit Ripeness", Angew. Chem. Int. Ed. 2012, No. 51, pp. 5752-5756.

European Search Report for European Application No. 20162159.6; Application Filing Date: Mar. 10, 2020; dated Aug. 10, 2020, 7 pages.

Fu et al., "Ultrasensitive Ethene Detector Based on Graphene-Copper(I) Hybrid Material", Nano Lett. 2017, No. 17, pp. 7980-7988.

Ojo et al., 2001, caplus an 2001:153627.

Ping et al., "Recent Advances in Sensing Applications of Two-Dimensional Transition Metal Dichalcogenide Nanosheets and Their Composites", Advanced Functional Materials, 2017, No. 27, 18 pages.

Reglinski et al., 1999, caplus an 1999:418573.

European Search Report for Application No. 20162037.4; dated Dec. 22, 2022; 5 Pages.

Kimblin et al: "Bis(mercaptoimidazolyl)(pyrazolyl)hydroborato Complexes of Zinc, Cadmium, and Cobalt: Structural Evidence for the Enhanced Tendency of Zinc in Biological Systems to Adopt Tetrahedral M[S4] Coordination"; Inorganic Chemistry, vol. 39, No. 19, Aug. 22, 2000, pp. 4240-4243.

Maffett et al.; "Nickel Nitrosyl Complexes in a Sulfur-Rich Environment: The First Poly(mercaptoimidazolyl)borate Derivative"; Elsevier; ScienceDirect; Polyhedron 26; pp. 4758-4764; Jun. 23, 2007.

Patel et al.; "Gold(I) Tris(mercaptoimidazolyl)borage Chmistry: Synthesis and Molecular Structure of the First Trinuclear TmR Complex of a Transition Metal"; Elsevier; ScienceDirect: Inorganic Chemistry Communications 9; pp. 748-750; Apr. 27, 2006.

Singaporean Written Opinion for Application No. 10202002246X; dated Nov. 25, 2022; 5 Pages.

White et al.; "Synthesis and Structural Characterization of 2-mercapto-1-tert-butylimidzole and its Group 12 Metal Derivatives (HmimtBu2MBr2 (M=Zn, Cd, Hg)"; Journal of Chemical Crystallography, vol. 33, Nos. 5/6, 9 Pages, Jun. 2003.

First Office Action issued by the China State IP Office Mar. 4, 2024 in corresponding Chinese patent application No. 202010161080.4, untranslated, 9 pages.

* cited by examiner

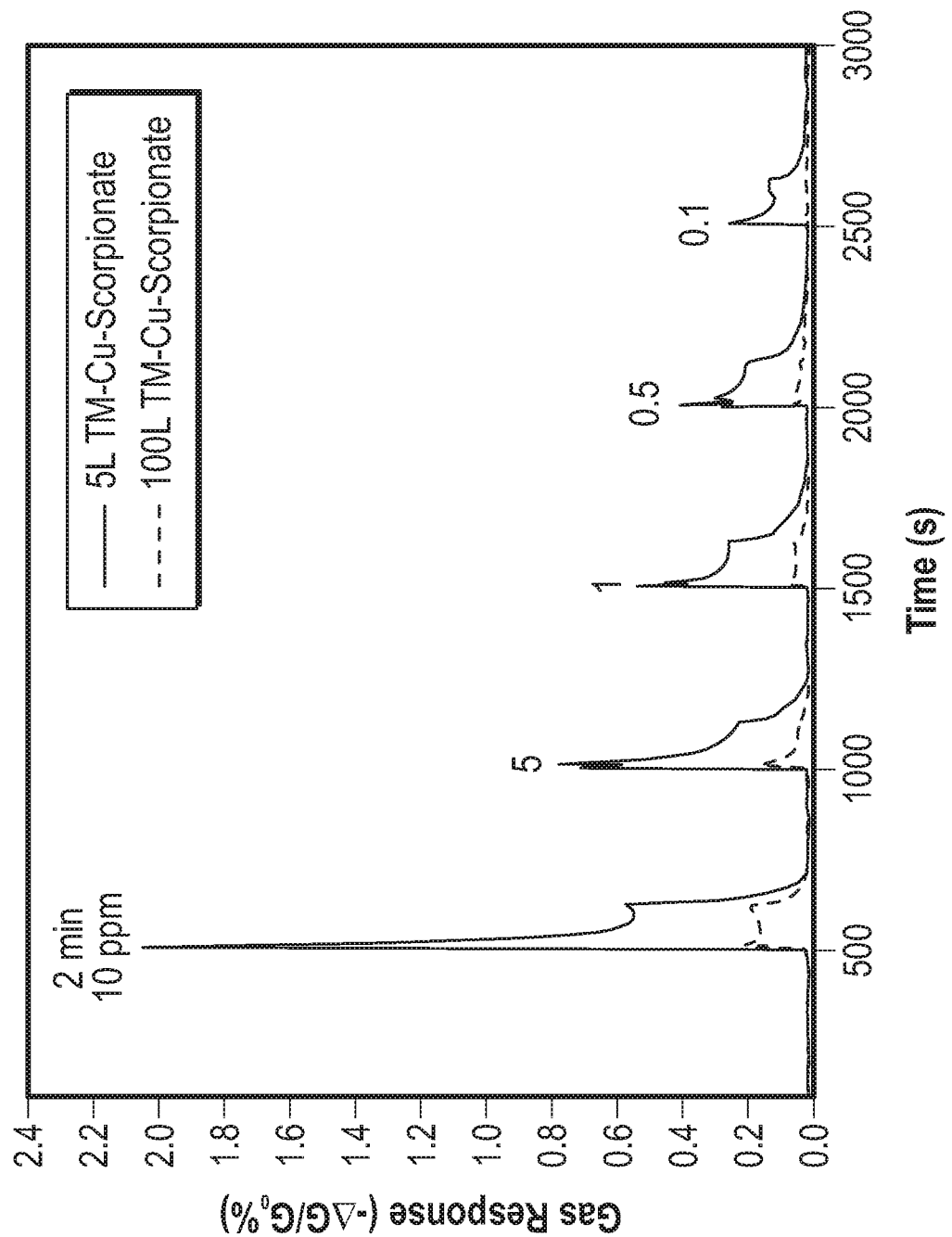

SENSOR FOR DETECTING GAS ANALYTE

CROSS REFERENCE TO RELATED APPLICATIONS

This application claims the benefit of U.S. Provisional Patent Application No. 62/816,662 filed on Mar. 11, 2019 which is incorporated by reference herein in its entirety.

BACKGROUND

Exemplary embodiments pertain to the art of sensor compositions based on metal-ligand complexes.

Volatile compounds with a double bond form an important group of compounds for detection. In particular, volatile alkenes, such as ethylene, are analytes of considerable importance. In particular, the detection of ethylene is important to industries related to produce and agriculture. Due to its small size and limited chemical functionality, however, ethylene is a challenging chemical analyte to detect. More efficient and sensitive methods of detection than those currently available are desired.

BRIEF DESCRIPTION

Disclosed is a sensor including a conductive region in electrical communication with two electrodes, the conductive region including single-walled carbon nanotubes, nanosized particles of a metal dichalcogenide, and a mercaptoimidazolyl metal-ligand complex.

In addition to one or more of the features described above, or as an alternative to any of the foregoing embodiments, the nanosized particles of a metal dichalcogenide include $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex includes more than one mercaptoimidazolyl group.

In addition to one or more of the features described above, or as an alternative to any of the foregoing embodiments, the mercaptoimidazolyl metal-ligand complex includes three mercaptoimidazolyl groups.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

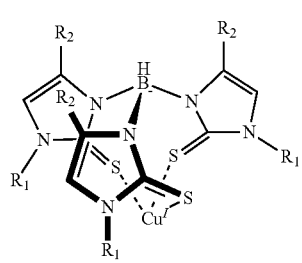

(II)

where each instance of $R_1$ and $R_2$ can be hydrogen or a group having one or more carbons.

Also disclosed is a method of sensing a volatile compound having a double or triple bond including exposing a sensor to a sample, the sensor including a conductive region in electrical communication with two electrodes, the conductive region including single-walled carbon nanotubes, nanosized particles of a metal dichalcogenide, and a mercaptoimidazolyl metal-ligand complex, and measuring an electrical property at the electrodes.

In addition to one or more of the features described above, or as an alternative to any of the foregoing embodiments, the electrical property is conductivity.

In addition to one or more of the features described above, or as an alternative to any of the foregoing embodiments, the electrical property is resistivity.

In addition to one or more of the features described above, or as an alternative to any of the foregoing embodiments, the method further includes comparing an electrical property value obtained by measuring to a calibration curve to determine the quantity of a volatile compound having a double or triple bond present in the sample.

In addition to one or more of the features described above, or as an alternative to any of the foregoing embodiments, the volatile compound having a double or triple bond is ethylene.

In addition to one or more of the features described above, or as an alternative to any of the foregoing embodiments, the nanosized particles of a metal dichalcogenide include $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex includes more than one mercaptoimidazolyl group.

In addition to one or more of the features described above, or as an alternative to any of the foregoing embodiments, the mercaptoimidazolyl metal-ligand complex includes three mercaptoimidazolyl groups.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

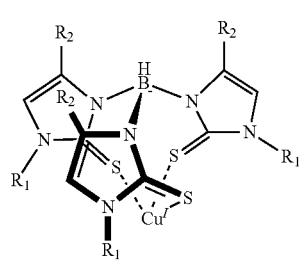

(II)

where each instance of $R_1$ and $R_2$ can be hydrogen, or a group having one or more carbons.

In another aspect, a method of preparing a sensor includes forming a conductive region including single-walled carbon nanotubes, nanosized particles of a metal dichalcogenide, and a mercaptoimidazolyl metal-ligand complex, and placing the conductive region in electrical communication with two electrodes.

BRIEF DESCRIPTION OF THE DRAWINGS

The following descriptions should not be considered limiting in any way. With reference to the accompanying drawing, like elements are numbered alike:

The FIGURE is a graph of the electrode signal plotted against gas concentration.

DETAILED DESCRIPTION

A detailed description of one or more embodiments of the disclosed apparatus and method are presented herein by way of exemplification and not limitation with reference to the FIGURE.

Volatile compounds with double or triple bonds are a group of important compounds for detecting and monitoring. The term volatile, as used herein, refers to compounds that are in the gas phase at standard temperature and pressure. Exemplary compounds include $NO_2$, $CO_2$, CO, and alkenes such as $C_2H_4$ (ethylene). As the hormone responsible for initiating the ripening of fruit as well as other processes in plant development, ethylene is an analyte of considerable importance to industries related to produce and agriculture. Due to its small size and limited chemical functionality, ethylene and other volatile alkenes are challenging chemicals to detect. Disclosed herein is a sensor and a method that is capable of detecting volatile compounds with double bonds such as ethylene and other volatile alkenes at levels down to 100 parts per billion (ppb).

The sensor includes a conductive region in electrical communication with at least two electrodes. The conductive region includes single-walled carbon nanotubes, nanosized particles of a metal dichalcogenide, and a mercaptoimidazolyl metal-ligand complex.

Single-walled carbon nanotubes are known materials and are commercially available. Exemplary materials include single-walled nanotubes available from NanoIntegris, US Research Nanomaterials, Inc., Millipore Sigma (formerly Sigma Aldrich), and NanoLab, Inc.

Metal dichalcogenides include transition metal dichalcogenides which are compounds formed from a Group 6B metal and a chalcogenide (S, Se, and Te). Exemplary metal dichalcogenides include $MoS_2$, $WS_2$, $MoSe_2$, $WSe_2$, $MoTe_2$, $WTe_2$, and combinations thereof. The metal dichalcogenide is in the form of nanosized particles. "Nanosized" as it applies to the metal dichalcogenides refers to the fact that the material has a thickness of less than or equal to 100 nanometers. The metal dichalcogenides are typically available in a flake form with a thickness of 100 nanometers or less although other physical forms are not excluded such as few-layer or single-layer materials, with the caveat that the physical form has at least one linear dimension that is less than or equal to 100 nanometers.

The mercaptoimidazolyl metal-ligand complex is a multidentate coordination complex comprising one or more mercaptoimidazolyl groups. The arms of the multidentate ligand (groups on the boron atom) can be the same (homoleptic) or different (heteroleptic). For example, one arm can comprise a mercaptoimidazolyl group and a second arm can comprise a pyrazolyl or indolyl group. It is also contemplated that a multidentate ligand may comprise more than one mercaptoimidazolyl group or a combination of mercaptoimidazolyl group(s) and pyrazolyl group(s) or indolyl groups or both. The mercaptoimidazolyl metal-ligand complex may have formula (I)

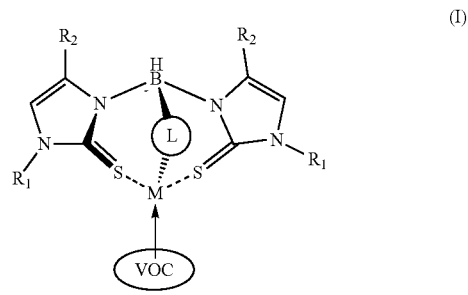

(I)

where each instance of $R_1$ and $R_2$ can be hydrogen or a group having one or more carbons. In some embodiments, each instance of $R_1$ and $R_2$ can be hydrogen or an alkyl group having 1 to 5 carbons. L in formula (I) can be a pyrazolyl group, a mercaptoimidazolyl group, or an indolyl. When L is a mercaptoimidazolyl group the multidentate metal-ligand complex can be described as homoleptic. When L is a group other than a mercaptoimidazolyl group the metal ligand complex can be described as a heteroleptic. VOC in formula I is present to show a postulated interaction with the volatile compound having a π bond. Without being bound by theory it is believed that the π bond of the volatile compound coordinates with an empty coordination site on the metal-ligand complex. The coordination alters the electronic configuration of the complex and can impact the electrical properties of the combination of the metal-ligand complex, nanosized particles of a metal dichalcogenide and metallic nanowires. In the case of a metal complex having formula II shown below, the resistivity of the combination of metal-ligand complex, nanosized particles of a metal dichalcogenide and metallic nanowires increases when the metal complex is bound to ethylene.

A more specific example of a mercaptoimidazolyl metal complex is shown in formula (II).

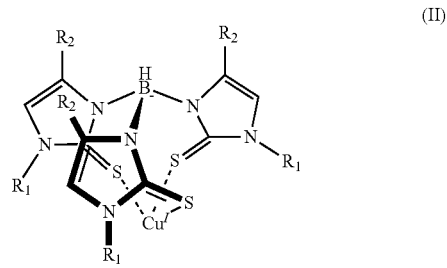

(II)

In formula (II) there are three mercaptoimidazolyl groups. $R_1$ and $R_2$ are defined as in formula (I).

The metal in the mercaptoimidazolyl metal complex may include Group 11 elements such as Cu(I), Ag(I), and Au(I).

The single-walled carbon nanotubes and nanosized particles of a metal dichalcogenide are applied to a substrate. The substrate may be a flexible polymer film or other suitable material. Exemplary flexible polymer films include polyethylene terephthalate, polyethylene, polypropylene, polyamide, and polyvinyl chloride. The electrodes may be deposited on the substrate before the application of the single-walled carbon nanotubes and nanosized particles of metal chalcogenide. The single-walled carbon nanotubes and nanosized particles of a metal chalcogenide may be applied by spray deposition. An example of a formulation that has been used to prepare working sensors is provided as Table 1. These materials are either co-deposited or sequentially deposited. After the single-walled carbon nanotubes and nanosized particles of a metal dichalcogenide are applied to the substrate the mercaptoimidazolyl metal-ligand complex is deposited on top of the single-walled carbon nanotubes and nanosized particles of a metal dichalcogenide. The mercaptoimidazolyl metal-ligand complex may be applied by drop casting, dip coating, spray coating, or by electrospray. The layered material is then dried and is ready for use.

TABLE 1

| | |
|---|---|
| H$_2$O | 91 wt % |
| iPrOH | 9 wt % |
| MoS$_2$ | 1.9 ppm |
| SWCNT | 2.5 ppm |
| sodium deoxycholate (surfactant) | <1 wt % |

A method of sensing a volatile compound having a double or triple bond includes exposing a sensor as described above to a sample and measuring an electrical property at the electrodes. The electrical property can be conductivity or resistivity. The method can also include comparing the obtained electrical property value to a calibration curve to determine the quantity of the volatile compound present in the sample.

The FIGURE shows data obtained using nanosized particles of MoS$_2$ in combination with single-walled carbon nanotubes as the underlayer. The underlayer was coated with mercaptoimidazolyl metal-ligand complex as shown in formula (II). The peaks are due to ethylene absorption (the samples used for ethylene exposure contained ethylene in amounts from 10 to 0.1 ppm).

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A sensor comprising a conductive region in electrical communication with two electrodes, the conductive region comprising single-walled carbon nanotubes, nanosized particles of a metal dichalcogenide, and a mercaptoimidazolyl metal-ligand complex, wherein the nanosized particles of a metal dichalcogenide comprise MoS$_2$, and wherein the mercaptoimidazolyl metal-ligand complex is a homoleptic complex of formula (II):

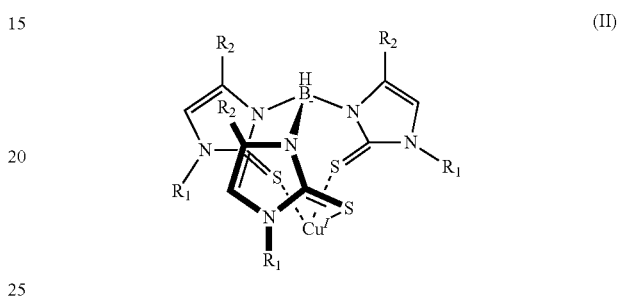

where each instance of R$_1$ and R$_2$ can be hydrogen, or a group having one or more carbons.

2. A method of sensing a volatile compound having a double or triple bond comprising exposing a sensor to a sample, the sensor comprising a conductive region in electrical communication with two electrodes, the conductive region including single-walled carbon nanotubes, nanosized particles of a metal dichalcogenide, and a mercaptoimidazolyl metal-ligand complex, and measuring an electrical property at the electrodes, wherein the nanosized particles of a metal dichalcogenide comprise MoS$_2$, and wherein the mercaptoimidazolyl metal-ligand complex is a homoleptic complex of formula (II):

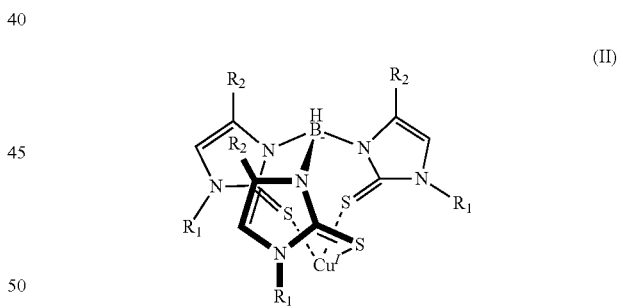

where each instance of R$_1$ and R$_2$ can be hydrogen, or a group having one or more carbons.

3. The method of claim 2, wherein the electrical property is conductivity.

4. The method of claim 2, wherein the electrical property is resistivity.

5. The method of claim 2, further comprising comparing an electrical property value obtained by measuring to a calibration curve to determine the quantity of a volatile compound having a double or triple bond present in the sample.

6. The method of claim 5, wherein the volatile compound having a double or triple bond is ethylene.

7. A method of preparing a sensor comprising forming a conductive region including single-walled carbon nanotubes, nanosized particles of a metal dichalcogenide, and a mercaptoimidazolyl metal-ligand complex, and placing the conductive region in electrical communication with two electrodes, wherein the nanosized particles of a metal dichalcogenide comprise $MoS_2$, and wherein the mercaptoimidazolyl metal-ligand complex is a homoleptic complex of formula (II):

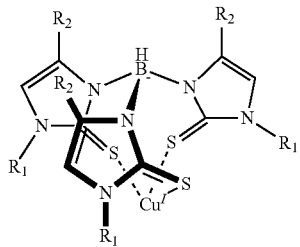

where each instance of $R_1$ and $R_2$ can be hydrogen, or a group having one or more carbons.

8. The method of claim 7, wherein forming the conductive region comprises applying the single-walled carbon nanotubes and the nanosized particles of the metal dichalcogenide to a substrate, and thereafter applying the mercaptoimidazolyl metal-ligand complex on top of the single-walled carbon nanotubes and the nanosized particles of the metal dichalcogenide.

9. The method of claim 8, wherein applying the mercaptoimidazolyl metal-ligand complex comprises drop casting, dip coating, spray coating, or by electrospray.

10. The sensor of claim 1, wherein the mercaptoimidazolyl metal-ligand complex is on top of the single-walled carbon nanotubes and the nanosized particles of the metal dichalcogenide.

* * * * *